(12) United States Patent
Zicker et al.

(10) Patent No.: US 8,592,478 B2
(45) Date of Patent: *Nov. 26, 2013

(54) ANTIOXIDANT-CONTAINING FOOD COMPOSITION

(75) Inventors: Steven Curtis Zicker, Lawrence, KS (US); Karen J. Wedekind, Meriden, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 316 days.

This patent is subject to a terminal disclaimer.

(21) Appl. No.: 11/154,210

(22) Filed: Jun. 16, 2005

(65) Prior Publication Data

US 2005/0232976 A1 Oct. 20, 2005

Related U.S. Application Data

(63) Continuation of application No. 09/978,132, filed on Oct. 16, 2001, now Pat. No. 6,914,071, which is a continuation-in-part of application No. 09/922,660, filed on Aug. 6, 2001, now abandoned.

(60) Provisional application No. 60/253,448, filed on Nov. 28, 2000, provisional application No. 60/244,504, filed on Oct. 31, 2000.

(51) Int. Cl.
*A23K 1/00* (2006.01)

(52) U.S. Cl.
USPC .............................. 514/440; 426/635; 426/805

(58) Field of Classification Search
USPC .................................................. 426/635, 805
See application file for complete search history.

(56) References Cited

U.S. PATENT DOCUMENTS

| | | | |
|---|---|---|---|
| 4,006,266 A | 2/1977 | Bone et al. | |
| 4,247,562 A | 1/1981 | Bernotavicz | |
| 4,883,672 A | 11/1989 | Shug et al. | |
| 5,006,361 A * | 4/1991 | Cox | 426/601 |
| 5,030,458 A * | 7/1991 | Shug et al. | 426/2 |
| 5,118,505 A | 6/1992 | Koltringer | |
| 5,292,538 A * | 3/1994 | Paul et al. | 426/74 |
| 5,339,771 A | 8/1994 | Axelrod | |
| 5,419,283 A | 5/1995 | Leo | |
| 5,569,670 A | 10/1996 | Weischer et al. | |
| 5,599,835 A | 2/1997 | Fischer | |
| 5,621,117 A | 4/1997 | Bethge et al. | |
| 5,728,735 A | 3/1998 | Ulrich et al. | |
| 5,730,988 A | 3/1998 | Womack | |
| 5,851,573 A * | 12/1998 | Lepine et al. | 426/74 |
| 5,883,083 A | 3/1999 | Harless | |
| 5,894,029 A | 4/1999 | Brown et al. | |
| 5,916,912 A * | 6/1999 | Ames et al. | 514/440 |
| 5,937,790 A * | 8/1999 | Ito et al. | 119/174 |
| 5,976,568 A | 11/1999 | Riley | |
| 5,977,162 A | 11/1999 | Seidman | |
| 5,981,767 A | 11/1999 | Tanner et al. | |
| 6,080,788 A | 6/2000 | Sole et al. | |
| 6,117,477 A | 9/2000 | Paluch | |
| 6,190,591 B1 | 2/2001 | van Lengerich | |
| 6,232,346 B1 * | 5/2001 | Sole et al. | 514/561 |
| 6,335,361 B1 * | 1/2002 | Hamilton | 514/440 |
| 6,365,211 B1 | 4/2002 | Corrigan | |
| 6,379,727 B1 | 4/2002 | Addy | |
| 6,426,362 B1 | 7/2002 | Miller et al. | |
| 6,479,069 B1 | 11/2002 | Hamilton | |
| 6,572,888 B2 | 6/2003 | Byrd | |
| 6,669,975 B1 | 12/2003 | Abene et al. | |
| 6,914,071 B2 * | 7/2005 | Zicker et al. | 514/440 |
| 7,282,225 B1 | 10/2007 | Davis et al. | |
| 2001/0028896 A1 | 10/2001 | Byrd | |
| 2001/0043983 A1 * | 11/2001 | Hamilton | 426/635 |
| 2001/0044448 A1 | 11/2001 | Dib | |
| 2002/0006907 A1 | 1/2002 | Gardiner et al. | |
| 2002/0076469 A1 | 6/2002 | Zicker et al. | |
| 2002/0076470 A1 | 6/2002 | Zicker et al. | |
| 2002/0115710 A1 | 8/2002 | Zicker et al. | |
| 2002/0119182 A1 | 8/2002 | Zicker et al. | |
| 2003/0035821 A1 | 2/2003 | Heaton et al. | |
| 2003/0044466 A1 | 3/2003 | Markey et al. | |
| 2003/0060503 A1 | 3/2003 | Hamilton | |
| 2003/0224061 A1 | 12/2003 | Pacioretty et al. | |
| 2004/0047896 A1 | 3/2004 | Malnoe et al. | |
| 2004/0068010 A1 | 4/2004 | Zicker et al. | |
| 2004/0166157 A1 | 8/2004 | Thombre | |
| 2005/0100617 A1 | 5/2005 | Malnoe et al. | |
| 2005/0123628 A1 | 6/2005 | Zabrecky | |
| 2005/0123643 A1 | 6/2005 | Cupp et al. | |
| 2008/0317725 A1 | 12/2008 | Baum | |
| 2009/0176864 A1 | 7/2009 | Zicker et al. | |

FOREIGN PATENT DOCUMENTS

| | | |
|---|---|---|
| CA | 2285490 | 4/2001 |
| CA | 2427692 | 5/2002 |
| CA | 2427261 | 6/2002 |

(Continued)

OTHER PUBLICATIONS www.PetsOnThePark.com.au/prod207.htm.*

(Continued)

*Primary Examiner* — Jeffrey S. Lundgren
*Assistant Examiner* — Chris Simmons
(74) *Attorney, Agent, or Firm* — Thomas M. Hunter

(57) ABSTRACT

A food composition comprises an antioxidant component comprising at least one of alpha-lipoic acid and L-carnitine, said composition meeting ordinary nutritional requirements for an adult canine or feline.

17 Claims, No Drawings

(56) References Cited

FOREIGN PATENT DOCUMENTS

| | | |
|---|---|---|
| CN | 1323165 A | 11/2001 |
| CN | 1829448 A | 9/2006 |
| CN | 101107012 | 1/2008 |
| DE | 19818563 | 10/1999 |
| EP | 0427247 | 5/1991 |
| EP | 1118332 | 7/2001 |
| EP | 1247456 | 10/2002 |
| EP | 1637041 | 3/2006 |
| EP | 1339292 | 12/2009 |
| JP | H2-49723 A | 2/1990 |
| JP | H10-042798 A | 2/1998 |
| JP | 2003-052338 A | 2/2003 |
| JP | 2003-261456 A | 9/2003 |
| JP | 2003-529347 | 10/2003 |
| JP | 2004-512053 | 4/2004 |
| JP | 2004-519241 | 7/2004 |
| JP | 2006-219467 | 8/2006 |
| JP | 2007-062326 | 3/2007 |
| JP | 2007-062332 | 3/2007 |
| JP | 2007-308468 | 11/2007 |
| JP | 2008-063234 | 3/2008 |
| JP | 2008-280322 A | 11/2008 |
| RU | 2071319 | 1/1997 |
| RU | 2099078 | 12/1997 |
| RU | 2303373 | 7/2007 |
| WO | 94/02036 * | 2/1994 |
| WO | WO98/04361 | 2/1998 |
| WO | WO98/41113 | 9/1998 |
| WO | WO 9843617 * | 10/1998 |
| WO | WO98/57627 | 12/1998 |
| WO | WO99/66913 | 12/1999 |
| WO | WO00/02553 | 1/2000 |
| WO | WO00/11968 | 3/2000 |
| WO | WO00/30666 | 6/2000 |
| WO | WO00/44375 | 8/2000 |
| WO | WO00/48594 | 8/2000 |
| WO | WO00/49891 | 8/2000 |
| WO | WO01/17366 | 3/2001 |
| WO | WO01/21208 | 3/2001 |
| WO | WO01/58271 | 8/2001 |
| WO | WO02/35943 | 5/2002 |
| WO | WO02/45525 | 6/2002 |
| WO | WO02/052955 | 7/2002 |
| WO | WO02/071874 | 9/2002 |
| WO | WO03/035056 | 5/2003 |
| WO | WO2005/006877 | 1/2005 |
| WO | WO2005/013714 | 2/2005 |
| WO | WO2005/058064 | 6/2005 |
| WO | WO2006/058248 | 6/2006 |
| WO | WO2006/058278 | 6/2006 |
| WO | WO2006/069241 | 6/2006 |
| WO | WO2006/071919 | 7/2006 |
| WO | WO2006/074089 | 7/2006 |
| WO | WO2007/009111 | 1/2007 |
| WO | WO2007/022344 | 2/2007 |
| WO | WO2007/063095 | 6/2007 |
| WO | WO2007/094669 | 8/2007 |
| WO | WO2007/149815 | 12/2007 |
| WO | WO2008/151131 | 12/2008 |
| WO | WO2010/083409 | 7/2010 |
| ZA | 9605149 A | 1/1997 |

OTHER PUBLICATIONS

Amazon.com: Hill's Science Diet Canine Senior (http://www.amazon.com/dp/B00063304U?smid=A2LDZGFAGG1QXE&tag=dealtime-pet-20&linkCode=asn).*
Epinions.com (http://www.epinions.com/review/Hill_s_Science_Diet_Canine_Senior/Pets-review-7CC1-752D32C-39779C59-prod4) (Jul. 2000).*
David Dzanis (J Nutr. Dec. 1994;124(12 Suppl):2535S-2539S).*
Sastre et al. (Free Radical Biology and Medicine vol. 24, Issue 2, Jan. 15, 1998, pp. 298-304 ).*
Packer et al. ("Packer"; Free Radical Biology & Medicine, vol. 19, No. 2, pp. 227-250, 1995).*
Anonymous, 2009, Dogs and Cats—Different Species, Different Needs, Retrieved from the internet http://www.felinefuture.com/?p=521, pp. 1-4.
AAFCO, 2003, Official Publication of the American Association of Feed Control Officials, p. 220.
AAFCO, 2004, American Association of Feed Control Officials Official Publication pp. 129-137.
Aksenova et al., 1999, "Oxidation of cytosolic proteins and expression of creatine kinase BB in frontal lobe in different neurodegenerative disorders," Dement. Geriatr. Cogn. Disord. 10(2):158-165.
Ames et al., 1993, "Oxidants, Antioxidants and the Degenerative Diseases of Aging," Proc. Natl. Acad. Sci. 90(17):7915-7922.
Ames, 1998, "Micronutrients Prevent Cancer and Delay Aging," Toxicol. Lett. 102-103:5-18.
Arivazhagan et al., 2000, "Antioxidant Lipoate and Tissue Antioxidants in Aged Rats," J. Nutr. Biochem. 11(3):122-127.
Arivazhagan et al., 2001, "Effect of DL-α-Lipoic Acid on the Status of Lipid Peroxidation and Antioxidants in Mitochondria of Aged Rats," J. Nutr. Biochem. 12:2-6.
Austad, 2008, "Advances in Vertebrate Aging Research 2007," Aging Cell 7(2):119-124.
Beckman et al., 1998, "Mitochondrial Aging: Open Questions," Annals NY Acad. Sci. 854:118-127.
Beckman et al., 1998, "The Free Radical Theory of Aging Matures," Physiol. Rev. 78(2):547-581.
Berkson, 1999, "A conservative triple antioxidant approach to the treatment of hepatitis C. Combination of alpha lipoic acid (thioctic acid), silymarin, and selenium: three case histories," Med. Klin 94(Suppl. 3):84-89 Medline AN: NLM10554539 Abstract.
Bezlepkin et al., 1996, "The prolongation of survival in mice by dietary antioxidants depends on their age by the start of feeding this diet," Mech. Ageing Dev. 92(2-3):227-234.
Bickford et al., 2000, "Antioxidant-rich diets improve cerebellar physiology and motor learning in aged rats," Brain Res. 866(1-2):211-217.
Blagosklonny, 2007, "An anti-aging drug today: from senescence-promoting genes to anti-aging pill," Drug Discovery Today 12(5/6):218-224.
Borras et al., 1999, "Age-related changes in the brain of the dog," Vet. Pathol. 36(3):202-211.
Branam, 1987, "Dietary Management of Geriatric Dogs and Cats," Vet. Tech. Vet. Learning Syst. 8(10):501-503.
Brigelius-Flohe et al., 1999, "Vitamin E: Function and Metabolism," FASEB J. 13:1145-1155.
Bruce-Keller et al., 1998, "4-Hydroxynonenal, a product of lipid peroxidation, damages cholinergic neurons and impairs visuospatial memory in rats," J. Neuropathol. and Exp. Neurol. 57(3):257-267.
Cantuti-Castelvetri et al., 2000, "Neurobehavioral Aspects of Antioxidants in Aging," Int. J. Develop. Neurosci. 18(4-5):367-381.
Cao et al., 1998, "Increases in Human Plasma Antioxidant Capacity after Consumption of Controlled Diets High in Fruit and Vegetables," Amer. J. Clin. Nutr. 68:1081-1087.
Caprioli et al., 1990, "Age-dependent deficits in radial maze performance in the rat: effect of chronic treatment with acetyl-L-carnitine," Prog. Neuro-Psychopharmacol. & Biol. Psychiat. 14(3):359-369.
Chandra, 2001, "Effect of vitamin and trace-element supplementation on cognitive function in elderly subjects," Nutrition 17(9):709-712.
Christen, 2000, "Oxidative stress and Alzheimer disease," Amer. J. Clin. Nutr. 71(2):621S-629S.
Coe, 2012, "Osteoarthritis in Dogs," http://www.vetbase.co.uk/information/osteoarthritis-dogs.php.
Cotman et al., 2002, "Brain Aging in the Canine: A Diet Enriched in Antioxidants Reduces Cognitive Dysfunction," Neurobiol. of Aging 23(5):809-818.
Crayhon, 1998, "Real Power of Antioxidants," Total Health 20(2):27-35.
Cummings et al., 1996, "The Canine As an Animal Model of Human Aging and Dementia," Neurobiol. of Aging 17:259-268.
Cutler, 1991, "Antioxidants and Aging," Amer. J. Clin. Nutr. 53(Suppl. 1):373S-379S.

(56) References Cited

OTHER PUBLICATIONS

Dictionary.com, 2012, Definition for "Prevent".
Dodd et al., 2003, "Can a Fortified Food Affect Behavioral Manifestations of Age-Related Cognitive Decline in Dogs?" Veterinary Medicine 98:396-408.
Droge, 2003, "Oxidative stress and aging," Adv. Exp. Med. Biol. 543:191-200.
Dunn, 2009, "Cats Are Different," Retrieved from the internet http://www.catsofaustralia.com/cat-nutrition.htm, p. 104.
Emmons, 1999, "Antioxidants to the Rescue," South Bend Tribune pp. 1-4.
Ernst, 1999, "Diet and Dementia, Is There a Link? A Systemati Review," Nutr. Neurosci. 2:1-6.
Estrada et al., 2001, "The Effects of Diet and Age on the Performance of the Landmark Discrimination Learning Task," 31st Ann. Meeting of Soc. for Neurosci., San Diego, CA 27(1):279, Abstract Biosis AN: PREV200100472166.
Frei, 1999, "Molecular and Biological Mechanisms of Antioxidant Action," FASEB J. 13:963-964.
Fryer, 1998, "Vitamin E Status and Neurodegenerative Disease," Nutritional Neurosci. 1(5):327-351.
Fuchs et al., 1994, "Antioxidant inhibition of skin inflammation induced by reactive oxidants: evaluation of the redox couple dihydrolipoate/lipoate," Skin Pharmacol. 7(5):278-284.
Fujimoto et al., 1989, "The effect of dietary docosahexaenoate on the learning ability of rats," in: Health Effects of Fish and Fish Oils, Chandra, ed., ARTS Biomedical Publishers and Distributors, St. John's, Newfoundland, pp. 275-284.
Gabbita et al., 1998, "Increased nuclear DNA oxidation in the brain in Alzheimer's disease," J. Neurochem. 71(5):2034-2040.
Grundman, 2000, "Vitamin E and Alzheimer disease: the basis for additional clinical trials," Amer. J. Clin. Nutr. 71(2):630S-636S.
Hagen et al., 1999, "(R)-alpha-lipoic acid-supplemented old rats have improved mitochondrial function, decreased oxidative damage, and increased metabolic rate," FASEB J. 13(2):411-418.
Han et al., 1997, "Lipoic acid increases de novo synthesis of cellular glutathione by improving cystine utilization," BioFactors 6(3):321-338.
Harman, 1961, "Prolongation of the normal lifespan and inhibition of spontaneous cancer by antioxidants," J. Gerontol. 16:247-254.
Harman, 1993, "Free Radical Theory of Aging: A Hypothesis on Pathogenesis of Senile Dementia of the Alzheimer's Type," Age 16:23-30.
Hawthorne, 2002, "Nutritional Requirements of Aging Dogs and Cats," Waltham Focus 12(1):28-34.
Head et al., 1995, "Spatial Learning and Memory as a Function of Age in the Dog," Behavioral Neurosci. 109(5):851-858.
Head et al., 2002, "A Longitudinal Dietary Antioxidant Intervention in Aged Canines Improves Learning and Reduces Peripheral Measures of Oxidative Damage," 32nd Annual Meeting of Soc. for Neurosci., Orlando, FL Biosis AN: PREV200300381007.
Hill et al., 2004, "Lipoic acid is 10 times more toxic in cats than reported in humans, dogs or rats," J. Animal Physiol. A. Animal Nutrition 88(3-4):150-156.
Ikeda-Douglas et al., 2004, "Prior Experience, Antioxidants, and Mitochondrial Cofactors Improve Cognitive Function in Aged Beagles," Vet. Ther. 5(1):5-16.
Information Network Village, 2011, Specialties (Agricultural Produce) http://www.invil.org/english/specialty/vegetable/potato/contents.j?con_no=602519&page_no-1.
International Search Report and Written Opinion in International Application No. PCT/US01/048495, mailed Jul. 30, 2002.
International Search Report and Written Opinion in International Application No. PCT/US01/049654, mailed Jul. 30, 2002.
International Search Report and Written Opinion in International Application No. PCT/US05/047192, mailed Jun. 14, 2000.
International Search Report and Written Opinion in International Application No. PCT/US06/027615, mailed Nov. 22, 2006.
International Search Report and Written Opinion in International Application No. PCT/US09/058244, mailed Dec. 14, 2009.
International Search Report and Written Opinion in International Application No. PCT/US09/068166, mailed May 7, 2010.
International Search Report and Written Opinion in International Application No. PCT/US09/068244, mailed Feb. 18, 2010.
International Search Report and Written Opinion in International Application No. PCT/US09/069686, mailed Nov. 12, 2010.
International Search Report and Written Opinion in International Application No. PCT/US10/041888, mailed Nov. 12, 2010.
Jayachandran et al., 1996, "Status of lipids, lipid peroxidation, and antioxidant systems with Vitamin C supplementation during aging in rats," J. Nutritional Biochem. 7(5):270-275.
Jones et al., 1997, "Evidence for the involvement of docosahexaenoic acid in cholinergic stimulated signal transduction at the synapse," Neurochemical Research 22(6):663-670.
Joseph et al., 2000, "Oxidative stress protection and vulnerability in aging: putative nutritional implications for intervention," Mechanisms of Ageing and Development 116(2-3):141-153.
Joseph, 2009, "Nutrition, Brain Aging, and Neurodegeneration," J. Neurosci. 29(41):12795-12801.
Kalaiselvi et al., 1998, "Effect of L-Carnitine on the Status of Lipid Peroxidation and Antioxidants in Aging Rats," J. Nutr. Biochem. 9:575-581.
Kealy et al., 2002, "Effects of diet restriction on life span and age-related changes in dogs," J. Amer. Vet. Med. Assoc. 220(9):1315-1320.
Keller et al., 1999, "4-hydroxynonenal increases neuronal susceptibility to oxidative stress," J. Neurosci. Res. 58(6):823-830.
Kim et al., 2006, "Antioxidant alpha-lipoic acid inhibits osteoclast differentiation by reducing nuclear factor-kappaB DNA binding and prevents in vivo bone resorption induced by receptor activator of nuclear factor-kappaB ligand and tumor necrosis factor-alpha," Free Radical Biol. & Med. 40(9):1483-1493.
Kolb et al., 1997, "Zum Bedarf an Vitaminen and an Ascorbinsaure beim Hund, mit Bemerkungen zur Publikation von M. Torel, TU51, 785-790, 996," Tieraerztliche Umschau 52(12):728-733.
Lee et al., 2004, "The impact of alpha-lipoic acid, coenzyme Q10 and caloric restriction on life span and gene expression patterns in mice," Free Radical Biol. Med. 36(8):1043-1057.
Leveque, 1998, "Cognitive Dysfunction in Dogs, Cats an Alzheimer's-Like Disease," J. Amer. Vet. Med. Assoc. 212(9):1351.
Liu et al., 1999, "Stress, aging, and brain oxidative damage," Neurochem. Res. 24(11):1479-1497.
Lovell et al., 1998, "Elevated 4-Hydroxynonenal in Ventricular Fluid in Alzheimer's Disease," Neurobiol. of Aging 18:457-461.
Lovell et al., 1999, "Increased DNA oxidation and decreased levels of repair products in Alzheimer's disease ventricular CSF," J. Neurochem. 72(2):771-776.
Markesbery et al., 1998, "Four-Hydroxnonenal, a Product of Lipid Peroxidation, Is Increased in the Brain in Alzheimer's Disease," Neurobiol. of Aging 19:33-36.
Markesbery et al., 1999, "Oxidative alterations in Alzheimer's disease," Brain Pathol. 9(1):133 146.
McGahon et al., 1999, "Age-related changes in oxidative mechanisms and LTP are reversed by dietary manipulation," Neurobiology of Aging 20(6):643-653.
McGahon et al., 1999, "Age-related changes in LTP and antioxidant defenses are reversed by an alpha-lipoic acid-enriched diet," Neurobiology of Aging 20(6):655-664.
McGahon et al., 1999, "Age-related changes in synaptic function: analysis of the effect of dietary supplementation with omega-3 fatty acids," Neuroscience 94(1):305-314.
Melder, 1982, "Modulation of natural killer cell activity in mice after interferon induction: depression of activity and depression of in vitro enhancement by interferon," Infect. Immun. 36(3):990-995.
Milgram et al., 1994, "Cognitive Functions and Aging in the Dog: Acquisition of Nonspatial Visual Tasks," Behavioral Neurosci. 108(1):57-68.
Milgram et al., 1999, "Landmark Discrimination Learning in the Dog," Learning & Memory 6(1):54-61.
Milgram et al., 2000, "Landmark Discrimination Learning in Aged Dogs Is Improved by Treatment with an Antioxidant Enriched Diet," Poster Presentation No. 193.9 at Society for Neuroscience Meeting New Orleans, LA.

(56) References Cited

OTHER PUBLICATIONS

Milgram et al., 2001, "Age Dependent Cognitive Dysfunction in Canines: Dietary Intervention," Proc. of the Third International Conference on Veterinary Behavioural Medicine, Overall, ed., Universities Federation for Animal Welfare, publisher pp. 53-57.
Milgram et al., 2002, "Dietary Enrichment Counteracts Age-Associated Cognitive Dysfunction in Canines," Neurobiol. of Aging 23(5):737-745.
Milgram et al., 2002, "Landmark Discrimination Learning in the Dog: Effects of Age, an Antioxidant Fortified Food, and Cognitive Strategy," Neurosci. Biobehav. Rev. 26(6):679-695.
Milgram et al., 2004, "Long-Term Treatment with Antioxidants and a Program of Behavioral Enrichment Reduces Age-Dependent Impairment in Discrimination and Reversal Learning in Beagle Dogs," Exp. Gerontol. 39(5):753-765.
Milgram et al., 2005, "Learning Ability in Aged Beagle Dogs is Preserved by Behavioral Enrichment and Dietary Fortification: A Two-Year Longitudinal Study," Neurobiology of Aging 26(1):77-90.
Milgram et al., 2007, "Acetyl-L-carnitine and alpha-lipoic acid supplementation of aged beagle dogs improves learning in two landmark discrimination tests," FASEB J. 21(13):3756-3762.
Nourhashemi et al., 2000, "Alzheimer disease: protective factors," Amer. J. Clin. Nutr. 71(2):643S-649S.
Packer et al., 1997, "Neuroprotection by the metabolic antioxidant alpha-lipoic acid," Free Radical Biol. & Med. 22(1-2):359-378.
Pastuszka et al., 2007, "Alpha-lipoic acid may be a clinically useful therapy in interstitial cystitis," Medical Hypotheses 69(4):957-958.
Patrick, 2000, "Nutrients and HIV: part three—N-acetylcysteine, alpha-lipoic acid, L-glutamine, and L-carnitine," Alt. Med. Review 5(4):290-305.
Perkins et al., 1999, "Association of antioxidants with memory in a multiethnic elderly sample using the Third National Health and Nutrition Examination Survey," Amer. J. Epidemiol. 150(1):37 44.
Petwave.com, 2012, "Treamtment [sic] & Prognosis of Renal Dysplasia in Dogs".
Podda et al., 1994, "Alpha-lipoic acid supplementation prevents symptoms of vitamin E deficiency," Biochem. Biophys. Res. Commun 204(1):98-104.
Pratico et al., 1998, "Increased F2-isoprostanes in Alzheimer's disease: evidence for enhanced lipid peroxidation in vivo," FASEB J. 12(15):1777-1783.
Pugh et al., eds., 2000, Stedman's Medical Dictionary, 27th Edition, Williams & Wilkins, p. 377.
Radak et al., 2001, "Regular exercise improves cognitive function and decreases oxidative damage in rat brain," Neurochem. International 38(1):17-23.
Riedel et al., 1998, "Nutrients, age and cognitive function," Curr. Opin. Nutr. Metab. Care 1(6):579-585.
Rogers, 2001, "A healthy body, a healthy mind: long-term impact of diet on mood and cognitive function," Proceedings of the Nutrition Society 60(1):135-143.
Rosenberg et al., 1959, "Effect of α-lipoic acid on vitamin C and vitamin E deficiencies," Arch. Biochem. Biophys. 80(1):86-93.
Roy et al., 1998, "Redox regulation of cell functions by alpha-lipoate: biochemical and molecular aspects," BioFactors 7(3):263-267.
Roy et al., 1998, "Redox regulation of cell functions by alpha-lipoate: biochemical and molecular aspects," BioFactors 8(1-2):17-21.
Ruehl et al., 1998, "Canine Cognitive Dysfunction," Ch. 13 in: *Psychopharmacology of Animal Behavior Disorders*, Wiley-Blackwekk, publisher, Dodman et al., eds., pp. 283-304.
Ruvo et al., 2000, "Nutritional antioxidants as antidegenerative agents," Int. J. Developmental Neurosci. 18(4-5):359-366.
Rybak et al., 1999, "Dose dependent protection by lipoic acid against cisplatin-induced ototoxicity in rats: antioxidant defense system," Toxicol. Sci. 47(2):195-202.
Sano et al., 1997, "A Controlled Trial of Selegiline, Alpha-Tocopherol, or Both as Treatment for Alzheimer's Disease. The Alzheimer's Disease Cooperative Study," New England J. Med. 336(17):1216-1222.
Savitha et al., 2005, "Oxidative stress on mitochondrial antioxidant defense system in the aging process: role of DL-alpha-lipoic acid and L-carnitine," Clinica Chimica Acta 355(1-2):173-180.
Schoenherr et al., 1997, "Nutritional modification of inflammatory diseases," Seminars in Veterinary Medicine and Surgery (Small Animal) 12(3):212-222.
Schupke et al., 2001, "New metabolic pathways of alpha-lipoic acid," Drug Metab. Dispos. 29(6):855-862.
Shigenaga et al., 1994, "Oxidative damage and mitochondrial decay in aging," PNAS 91(23):10771-10778.
Siwak et al., 2000, "Age-associated changes in non-cognitive behaviors in a canine model of aging," Soc. Neurosci. 26(2):2332, Abstract No. 873.3.
Siwak et al., 2005, "Chronic antioxidant and mitochondrial cofactor administration improves discrimination learning in aged but not young dogs," Progress in Neuro-Psychopharmacol. Biological Psychiatry 29(3):461-469.
Siwak et al., 2003, "Locomotor Activity Rhythms in Dogs Vary with Age and Cognitive Status," Behavioral Neurosci. 117(4):813-824.
Socci et al., 1995, "Chronic antioxidant treatment improves the cognitive performance of aged rats," Brain Research 693(1-2):88-94.
Stoll et al., 1993, "The potent free radical scavenger alpha-lipoic acid improves memory in aged mice: putative relationship to NMDA receptor deficits," Pharmacol. Biochem. & Behavior 46(4):799-805.
Stoll et al., 1994, "The potent free radical scavenger alpha-lipoic acid improves cognition in rodents," Ann. NY Acad. Sci. 717:122-128.
Syufy, 2007, "Q. How Long Is the Common Cat Supposed to Live?" http://cats.about.com/cs/catmanagement101/f/lifespan_cats.htm website retrieved Nov. 12, 2007.
Tapp et al., 2003, "An Antioxidant Enriched Diet Improves Concept Learning in Aged Dogs," 33rd Annual Meeting of Soc. for Neurosci., New Orleans, LA Biosis AN: PREV200400205135.
Tsokos et al., 1982, "Natural killer cells and interferon responses in patients with systemic lupus erythematosus," Clin. Exp. Immunol 50(2):239-245.
Vancouver Vets, 2011, "Osteoarthritis in Dogs. Treatment & Prognosis" www.articlesbase.com/print/5146156.
Vazour, 2012, "Dietary Polyphenols as Modulators of Brain Functions: Biological Actions and Molecular Mechanisms Underpinning Their Beneficial Effects," Oxidative Med. and Cell. Longevity vol. 2012, Article ID: 914273, 16 pgs.
Villeponteau et al., 2000, "Nutraceutical interventions may delay aging and the age-related diseases," Exp. Gerontol. 35(9-10):1405-1417.
Weaver et al., 1988, "Health effects and metabolism of dietary eicosapentaenoic acid," Prog. Food Nutr. Sci. 12(2):111-150.
Youdim et al., 2000, "Essential fatty acids and the brain: possible health implications," Int. J. Devel. Neurosciences 18(4-5):383-399.

\* cited by examiner

ANTIOXIDANT-CONTAINING FOOD COMPOSITION

RELATED APPLICATIONS

This application is a continuation of application Ser. No. 09/978,132 filed Oct. 16, 2001, which is a continuation-in-part of application Ser. No. 09/922,660 filed Aug. 6, 2001, which claims benefit of Provisional Application Ser. No. 60/253,448 filed Nov. 28, 2000 and Provisional Application Ser. No. 60/244,504, filed Oct. 31, 2000.

BACKGROUND OF THE INVENTION

Companion animals such as dogs and cats seem to suffer from aging problems. Some of these are manifested in commonplace sayings. One of these is "You can't teach an old dog new tricks." This saying arises from the observation that as dogs age, their mental capacity seems to diminish as well as physical abilities. Mental activities associated with thinking, learning and memory seem to be lessened (Cummings, B. J., Head, E., Ruehl, W., Milgram, N. W. & Cotman, C. W. (1996): The canine as an animal model of aging and dementia. Neurobiology of Aging 17:259-268). Additionally, behavioral change can be manifested in the aging animals in association with the changing mental capacity. Many causes have been assigned to this lessening of capacity.

These losses in capacity are generally observed in aged canines and felines. Dogs of seven years or older and felines of seven years or older are considered aged and can experience this problem.

The presence of significant levels of at least one antioxidant in the diet of an adult companion pet or fed to a pet outside his diet can inhibit the onset of deterioration of the mental capacity of the aged companion pet and/or maintain the mental capacity of the adult companion pet further into the aged years.

SUMMARY OF THE INVENTION

In accordance with the invention, there is a companion pet diet meeting ordinary nutritional requirements of an adult pet and further comprising a sufficient amount of an antioxidant or mixture thereof to inhibit the onset of deterioration of the mental capacity of said companion pet in its aged years.

A further aspect of the invention is a method for inhibiting the deterioration of the mental capacity of an aged companion pet, which comprises feeding said pet in his adult years an antioxidant or mixture thereof at sufficient levels to accomplish this inhibition.

In further accordance with the invention is a companion adult pet diet meeting ordinary nutritional requirements as proposed by the American Association of Feed Control Officials (AAFCO 2002) of an adult companion pet and further comprising an antioxidant selected from the group consisting of Vitamin E, vitamin C, alpha-lipoic acid, 1-carnitine and any mixtures thereof in quantities sufficient to inhibit the deterioration of the mental capacity of said pet in its aged years.

A still further aspect of the invention is a method for increasing the mental capacity of an aged companion pet, which comprises feeding the pet in its adult years an amount of an antioxidant or mixture thereof sufficient to increase the mental capacity.

Another aspect of the invention is a method for increasing the mental capacity of an adult companion pet which comprises feeding the pet an amount of an antioxidant or mixture thereof sufficient to increase the mental capacity of said pet.

In all of these methods, it is desirable to administer the antioxidant or mixture thereof in the diet of the animal.

DETAILED DESCRIPTION OF THE INVENTION

The diet fed to the adult companion pet, for example canine and feline, is the standard normal diet fed to an animal of that age. Below is a typical diet for a canine of 1 to 6 years of age.

TABLE 1

| Component | Target |
| --- | --- |
| Protein (% of dry matter) | 23 |
| Fat (% of dry matter) | 15 |
| Phosphorus (% of dry matter) | 0.6 |
| Sodium (% of dry matter) | 0.3 |

Adding significant quantities of an antioxidant or mixture thereof to the companion adult pet diet can bring about delay of the onset of demonstrative changes in the behavior, particularly the deterioration of mental capacity, as specifically shown by problem-solving capacity, in an aged pet. The term, adult, is intended to mean, in general, a canine of at least 1 to 6 years and a feline of at least 1 to 6 years. An aged dog or cat is 7 years and above.

The loss of mental capacity for canines and felines has been observed for a number of years. This loss of mental capacity is manifested in numerous ways. For a canine, for example, it can be manifested as disorientation, house soiling, altered sleep-wake patterns, decreased or altered interaction with humans and other pets, and inability to learn and concentrate. These conditions can be manifested in felines as well. Alzheimer's, as exhibited in man, is not found in canines and felines.

Many theories have been advanced for this loss in mental capacity. To date, the inventors are unaware of any dietary course of action, which inhibits this loss of mental capacity or can actually bring about a positive change in mental capacity as measured by an objective parameter in dogs and cats.

The inventors have succeeded in accomplishing delaying the onset of this deterioration. By using the diet of their invention in adult companion pets it can be shown that aged pets' mental capacity can be maintained for a longer period of time. Essentially the deterioration of mental capacity can be stopped or delayed. Memory and learning ability can be improved. Overall mental alertness can be enhanced. Age related cognitive decline could be slowed. With respect to Cognitive Dysfunction Syndrome its progress can be slowed in aged dogs and clinical signs associated with this syndrome can be controlled. Prophylaxis where appropriate and pets in need of these components are the target group.

The component in the diet which accomplishes this is an antioxidant or mixture thereof. An antioxidant is a material that quenches a free radical. Examples of such materials include foods such as *ginkgo biloba*, citrus pulp, grape pomace, tomato pomace, carrot and spinach, all preferably dried, as well as various other materials such as beta-carotene, selenium, coenzyme Q10 (ubiquinone), lutein, tocotrienols, soy isoflavones, S-adenosylmethionine, gluthathione, taurine, N-acetylcysteine, vitamin E, vitamin C, alpha-lipoic acid, L-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The D form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like, which will function in a vitamin C like activity after ingesting by the pet. They can be in any form such as liquid, semisolid, solid and heat stable form. Alpha-lipoic acid can be administered into the diet as alpha-lipoic acid or as a lipoate derivative as in U.S. Pat. No. 5,621,117, racemic mixtures, salts, esters or amides thereof. L-carnitine can be administered in the diet and various derivatives of carnitine such as the salts such as the hydrochloride, fumarate and succinates, as well as acetylated carnitine and the like, can be used.

The quantities administered in the diet, all as wt % (dry matter basis) of the diet, are calculated as the active material, per se, that is measured as free material. The maximum amounts employed should not bring about toxicity. At least about 100 ppm or at least about 150 ppm of vitamin E can be used. A preferred range of about 500 to about 1,000 ppm can be employed. Although not necessary a maximum of about 2,000 ppm or about 1,500 ppm is generally not exceeded. With respect to vitamin C at least about 50 ppm is used, desirably at least about 75 ppm and more desirably at least about 100 ppm. A nontoxic maximum can be employed. The quantity of alpha-lipoic acid can vary from at least about 25, desirably at least about 50 ppm, more desirably about 100 ppm. Maximum quantities can vary from about 100 ppm to 600 ppm or to an amount which remains nontoxic to the pet. A preferred range is from about 100 ppm to about 200 ppm. For L-carnitine about 50 ppm, desirably about 200 ppm, more desirably about 300 ppm for canines are a useful minimum. For felines, slightly higher minimums of L-carnitine can be employed such as about 100 ppm, 200 ppm, and 500 ppm. A nontoxic maximum quantity can be employed, for example, less than about 5,000 ppm. For canines, lower quantities can be employed, for example, less than about 5,000 ppm. For canines a preferred range is about 200 ppm to about 400 ppm. For felines a preferred range is about 400 ppm to about 600 ppm.

Beta-carotene at about 1-15 ppm can be employed.
Selenium at about 0.1 up to about 5 ppm can be employed.
Lutein: at least about 5 pm can be employed.
Tocotrienols: at least about 25 ppm can be employed.
Coenzyme Q10: at least about 25 ppm can be employed.
S-adenosylmethionine: at least about 50 ppm can be employed.
Taurine: at least about 1000 ppm can be employed.
Soy isoflavones: at least about 25 ppm can be used.
N-acetylcysteine: at least about 50 ppm can be used.
Glutathione: at least about 50 ppm can be used.
*Gingko biloba*: at least 50 ppm of extract can be used.

The following are raw ingredients that are high in ORAC (Oxygen radical absorbing capacity) content. When added to the diet as 1% inclusions (for a total of 5% substitution for a low ORAC ingredient such as corn) they increased the ORAC content of the overall diet and increased the ORAC content of the plasma of the animals which ate the diet containing these components. Preferably, any ingredient with an ORAC content >25 μmole of Trolox equivalents per gram of dry matter could be used if added at 1% in combination with four other 1% ingredients for a total of 5% addition to the diet.

Spinach pomace
Tomato pomace
Citrus pulp
Grape pomace
Carrot granules
Broccoli
Green tea
*Ginkgo biloba*
Corn gluten meal Example 1

Seventeen adult beagle dogs 2-4 years of age (control n=8, antioxidant-enriched n=9) were randomly placed into a control or enriched diet group. The control diet contained 59 ppm vitamin E and <32 ppm vitamin C. The test diet had 900 ppm vitamin E and 121 ppm vitamin C, 260 ppm L-carnitine and 135 ppm alpha-lipoic acid. Approximately 1 month after starting the diet, the first problem-solving task given to dogs was a landmark discrimination learning task, which is a test of spatial attention (Milgram, N. W., Adams, B., Callahan, H., Head, E., Mackey, B., Thirlwell, C. & Cotman, C. W. (1999): Landmark discrimination learning in the dog. Learning & Memory, 6:54-61).

Landmark discrimination learning requires subjects to select a particular object based on proximity to an object. The initial learning, however, is based on the dogs' ability to learn an object discrimination task. We have previously found that the effects of age on discrimination learning depend on task difficulty.

The adult dogs on the enriched diet made fewer errors than the adult dogs on the control food when learning the landmark O test (control mean=31.1, enriched mean=15.1). The adult dogs proceeded on to landmark 1 and 2 testing, where the landmark is moved further away from the positive well. Adult dogs on enriched diet learned landmark 0-2 with less errors than those on the control (number of mean errors landmark 0+1+2 (control)=132.9; number of mean errors landmark 0+1+2 (dogs on enriched diet)=87.1).

Example 2

30 adult, random source, dogs were utilized for this study. Dogs were at least 10 months of age, not pregnant, not lactating and of reasonable body weight prior to start of test. Animals were randomized into 5 groups for dietary treatment with 3 males and 3 females per each group.

All dogs were fed a control food (0 ppm DL-alpha-lipoic acid added) that met or exceeded all recommendations for nutrients as proposed by the American Association of Feed Control Officials (AAFCO 2000) during a 2 week prefeeding period (Table 1). Following the prefeeding period dogs were randomized into 5 treatment groups with one of the following DL-alpha-lipoic acid target inclusions (dry matter basis): 0 ppm, 150 ppm, 1,500 ppm, 3,000 ppm, 4,500 ppm. In all diets, control and alpha-lipoic acid, vitamin E was added and was present at a level of 600-1000 International Units, and vitamin C was added at levels of 100-200 ppm.

Test foods were the sole source of nutrients except for water. Fresh water was provided ad libitum. After dogs were selected and initial body weights taken, a food dose was calculated for each dog based on the expected ME of the food. Initial food dose calculations were based on the maintenance energy requirement (MER) for the dog modified by a factor to account for normal activity as calculated by the following formula:

$$MER(kcal/day)=1.6 \times RER(\text{Resting Energy Requirement})$$

where: RER (kcal/day)=$70 \times$body weight $(kg)^{0.75}$.

Dogs were weighed weekly and had food doses adjusted as needed in order to feed enough food to maintain their optimal body weight. Optimal body weight was determined to be 3 on a 5 point scale. If a dog did not maintain body weight within −10% of initial body weight, after adjustment of food dose, it was removed from the study. All measures of body weight and food intake were recorded.

Samples were ground and 0.100±0.001 g of sample was extracted twice into 5.0 ml phosphate buffer (10 mM $Na_2HPO_4$, 2 mM ethylenediaminetetraacetic acid (EDTA), 0.9% NaCl, pH 7.4). 250 µl of extract was placed into a 5 ml glass centrifuge tube with a Teflon lined cap. 15 µl EDTA solution (100 mM EDTA, adjusted to pH 7.8 with ~1M NaOH) and 50 µl freshly prepared 5 mM dithioerythritol (DTE) were added. The solutions were vortexed and incubated at room temperature for 5 minutes. Then 10 µl of 1M $H_3PO_4$ and 2.0 ml diethyl ether were added. The tubes were capped, vortexed, and centrifuged at 1500×g for 3 minutes at room temperature. The ether layer was transferred to a separate 5 ml glass centrifuge tube, while the aqueous layer was extracted twice more with 1.5 ml ether. All extractions from the same sample were combined. The extracts are then dried in a nitrogen evaporator in a water bath at room temperature. At this point, the samples were capped and frozen overnight.

The dried extracts were then thawed and reconstituted with 70 µl SDS/EDTA solution (0.11% sodium dodecyl sulfate (SDS), 15 mM EDTA, 0.9% NaCl) and 5 µl freshly prepared 1 mM DTE. 50 µl of freshly prepared $NaBH_4$ was then added to each tube. The tubes were vortexed and incubated at room temperature for 10 minutes. After 10 minutes, the samples were frozen at −70° C. Before the solutions were thawed, 20 µl 2 M HCl was added. After the solutions were thawed, 800 µl 100 mM $NH_4HCO_3$ was added. The solutions are vortexed and 5 µl of 100 mM monobromobimane in acetonitrile solution (mBBr) was added. The solutions were then incubated in the dark for 90 minutes at room temperature.

Excess mBBr and the DTE derivative were removed from the samples after incubation by extraction with 1.5 ml dichloromethane. The aqueous layer was placed on the HPLC. The lipoic acid was separated using a mobile phase that consisted of 30% acetonitrile, 1% acetic acid, adjusted to pH 3.95 with ~2 M $NH_4OH$ and was pumped at a flow rate of 1.0 ml/min with an isocratic elution for 15 minutes per injection. This preparation assumes that the density of the extruded food is equal to 1 g/ml.

Blood was collected aseptically for complete blood count and blood biochemistry analysis 2 weeks prior to start, and again at 0, 28, 56, 84, 112, 140 and 168 days of the study. In addition, 15 ml of whole blood was collected for isolation of lymphocytes at days 0, 28 and 84 of the dietary intervention.

Heparinized whole blood was layered onto a 50 ml Accuspin conical centrifuge tube (Sigma Chemical) and an equal volume of phosphate buffered saline (PBS) was added. Samples were centrifuged at 700×g for 30 minutes without brake. The monocyte layer was harvested, transferred to a 15 ml conical centrifuge tube, resuspended in 1-3 ml of PBS, and centrifuged as before (first wash). A second wash was performed as the first wash. Finally, cells were harvested and suspended in perchloric acid (10% w/v) and frozen at 70° C. until analysis.

Samples were transferred from −70° C. freezer into a cooler with dry ice in it. Vials were centrifuged at 12,000 rpm for 5 minutes in a refrigerated centrifuge. An aliquot of supernatant for glutathione (GSH) analysis was transferred to a conical test tube.

Derivatization of the acid soluble extracts was by the method of Reed and coworkers (Fariss et al) as modified by Jones (Jones et al).

Briefly, 150 µl extract or external standards were added into a 1.5 ml eppendorf tube followed by addition of 20 µl γ-glu-glu internal standard and 50 µl IAA added followed by mixing. The solution was adjusted to pH ~10 (purple color) by using KOH—$KHCO_3$ working solution. Solutions were incubated 1 hr under room temperature in the dark. Sanger's reagent was added at the same volume as of the total volume and the solution was incubated overnight (20 hrs) in the dark at room temperature.

After incubation, the solution was centrifuged at 12,000 rpm for 5 minutes with the supernatant transferred into another 1.5 ml eppendorf tube. 200 µl supernatant was added into an amber autovial which had a 300 µl inlet, fix the top with a crimper for HPLC analysis.

Solvents and separation conditions were as described (Fariss, Jones). Levels of GSH and GSSG were quantified relative to authentic standards. Gamma-glutamyl-glutamate was used as an internal standard to assess derivatization efficiency.

Comparison of values for clinical chemistry, hematology and body weights vs baseline were analyzed by way of paired t-test on SAS for Windows with significance set at $P<0.05$. Means of values at each measured time point were separated by a one-way ANOVA with significance set at $P<0.05$. The difference in GSH:GSSG between day 84 and baseline were analyzed between groups by way of SAS for Windows in a one-way ANOVA with significance set at $P<0.05$.

Results

Concentrations of lipoic acid (ppm) in food as determined over 7 successive assays (0, 28, 56, 84, 112, 140, 168 days) were within the range of expected assay sensitivity and production parameters typically encountered at our facility (Table 2).

The food intake data were unremarkable. Most animals in all groups ingested more food at 6 months, on average, than at the beginning of the study. Body weight data were unremarkable except that some weight loss occurred initially in the 4,500 ppm inclusion group but that change appeared to reverse by 6 months time. Body condition scores did not appear to be affected by this minor loss of weight.

The routine physical examinations did not reveal any evidence of nutrition related abnormalities or DL-alpha-lipoic acid toxicity. All animals in the study population remained normal during the entire course of the study. Occasional vomiting was observed in several animals during the course of the study; however, a trend was not observed that would lead one to the conclusion that the vomiting may be attributable to lipoic acid. One animal, in the highest inclusion group, was dropped from the study at day 21 for weight loss and leukocytosis. The leukocytosis in this animal had not resolved by the end of the study and is suspected to be attributable to some other disease process.

When serum biochemistry values for days 28, 56, 84, 112, 140, and 168 were compared with the initial values for the same group of dogs, several statistical differences were noted, however, none of these were considered biologically significant because these values were within or very near the laboratory reference range and consistent trends over months were noted. Comparisons between the controls and the other treatment groups at each time period also revealed several statistical differences, however, none of these were considered biologically significant because these values were within or very near the clinical laboratory reference ranges and no trends were present.

When the hematology values for days 28, 56, 84, 112, 140 and 168 were compared with the initial values for the same group of dogs, several statistical differences were noted; however, none of these were considered biologically significant because these values were within or very near the laboratory reference range and no trends were present. Comparison between the controls and the other treatment groups at each time period revealed several statistical differences; however, none of these were considered biologically significant because these values were within or very near the clinical laboratory reference ranges and no trends were present.

GSH:GSSG Ratio

The change in GSH:GSSG ratio over 84 days of feeding displayed a significant overall effect of diet (P=0.024) with all supplemented groups having an increase in the ratio (Table 3). ANOVA revealed a significant difference, compared to the basal food, for the lowest and highest inclusions, however, the largest numerical increase was in the lowest inclusion level. That is to say, the changes in the GSH:GSSG ratio for the highest and lowest inclusion were significantly different from the change observed over this same time period in the basal food. Ratios for 4 points could not be determined at day 84 as no GSSG was detectable in any of these samples (1 control, 3 treatment groups). As such, the values for supplemented groups may have displayed even higher ratios of GSH:GSSG if the assay had been sensitive enough to detect the low levels of GSSG at day 84.

TABLE 2

| Inclusion Rate (ppm) | Average | Standard Deviation | Percent Target |
|---|---|---|---|
| 0 | 24 | 17 | NA |
| 150 | 151 | 13 | 101 |
| 1,500 | 1471 | 113 | 98 |
| 3,000 | 2869 | 250 | 96 |
| 4,500 | 4176 | 642 | 93 |

TABLE 3

Change in mean ratio of GSH:GSSG from day 0 to day 84 in dogs consuming DL-alpha lipoic acid in an extruded food

| Inclusion | Difference in GSH:GSSG ratio - day 0 to day 84 compared to baseline food | N | P value |
|---|---|---|---|
| 0 ppm | −9.2 ± 26 | 5* | NA |
| 150 ppm | 70 ± 20 | 6 | 0.003 |
| 1,500 ppm | 24 ± 7 | 6 | 0.16 |
| 3,000 ppm | 10 ± 4 | 4* | 0.46 |
| 4,500 ppm | 50 ± 36 | 4* | 0.03 |

*1 dog in the control and 4,500 ppm group had no detectable GSSG at day 84 while 2 dogs in the 3,000 ppm group had no detectable GSSG at day 84.

Further observations with respect to alpha-lipoic acid are applicable. Chronic feeding of alpha-lipoic acid in diet is safe and effective. It improves the reduced glutathione (GSH) to oxidized glutathione (GSSG) ratio. The chronic administration of alpha-lipoic acid in the diet can be for periods of one, two, three, four, five, or six months minimum up through a period of one, two, three, four, five years or even more including the lifetime of the animal. The alpha-lipoic acid functions without any special protection in the diet such as encapsulation and need not be present in the diet in a unit dosage form such as those used in pharmaceuticals, for example, tablet, pill, capsule and the like. The lipoic acid is provided in the diet in a minimum of about 25, 50, 75, or 100 ppm of diet. The uppermost range is just below its toxic level, all the way down to about 400, 300, or 200 ppm of diet. Generally, one does not go beyond about 6 or 7 mg/kg body weight of animal per day, more generally not above about 5. The alpha-lipoic acid improves antioxidant defense capabilities as well as improves the animal's ability to resist oxidative damage. All this is done with the proper quantities of other antioxidants present such as vitamin E and vitamin C. This demonstrates that the action of alpha-lipoic acid is beyond that of vitamin C and/or vitamin E.

What is claimed is:

1. A companion animal pet food composition comprising an antioxidant component that comprises alpha-lipoic acid, said companion animal pet food composition suitable for an adult canine or feline, wherein the alpha-lipoic acid is present in the pet food in an amount from about 100 ppm to 600 ppm by weight on a dry matter basis, and wherein said companion animal pet food composition meets the ordinary nutritional requirements as a sole diet for an adult canine or feline.

2. The composition of claim 1, further comprising L-carnitine.

3. The composition of claim 1, wherein alpha-lipoic acid is present in an amount of about 100 ppm to about 200 ppm on a dry matter basis.

4. The composition of claim 2, wherein L-carnitine is present in an amount of about 50 ppm to about 5000 ppm, and wherein the composition meets ordinary nutritional requirements for an adult canine.

5. The composition of claim 4, wherein the L-carnitine is present in an amount of about 200 ppm to about 400 ppm.

6. The composition of claim 2, wherein L-carnitine is present in an amount of about 100 ppm to about 5000 ppm, and wherein the composition meets ordinary nutritional requirements for an adult feline.

7. The composition of claim 6, wherein the L-carnitine is present in an amount of about 400 ppm to about 600 ppm.

8. The composition of claim 1, wherein the antioxidant component further comprises at least one of vitamin E and vitamin C.

9. The composition of claim 8, wherein vitamin E is present in an amount of about 100 ppm to about 2000 ppm.

10. The composition of claim 8, wherein vitamin E is present in an amount of about 500 ppm to about 1000 ppm.

11. The composition of claim 8, wherein vitamin C is present in an amount of at least 50 ppm.

12. The composition of claim 8, wherein vitamin C is present in an amount of at least 100 ppm.

13. The composition of claim 1, wherein the antioxidant component further comprises a material selected from the group consisting of beta-carotene, selenium, coenzyme Q10, lutein, tocotrienols, soy isoflavones, S-adenosylmethionine, glutathione, taurine, N-acetylcysteine and combinations thereof.

14. The composition of claim 1, wherein the antioxidant component is supplied at least in part by an ingredient having an oxygen radical absorbing capacity of greater than 25 micromole of 6-hydroxy-2,5,7,8-tetramethylchroman-2-carboxylic acid equivalents per gram of dry matter.

15. The composition of claim 14, wherein the ingredient having an oxygen radical absorbing capacity of greater than 25 micromole of 6-hydroxy-2,5,7,8-tetramethylchroman-2-carboxylic acid equivalents per gram of dry matter is selected from the group consisting of spinach pomace, tomato pomace, citrus pulp, grape pomace, carrot granules, broccoli, green tea, *ginkgo biloba*, corn gluten meal and combinations thereof.

16. A companion animal pet food composition comprising an antioxidant component that comprises (a) alpha-lipoic acid in an amount of about 100 ppm to about 200 ppm, (b) L-carnitine in an amount of about 200 ppm to about 400 ppm, (c) vitamin E in an amount of about 500 ppm to about 1000 ppm, and (d) vitamin C in an amount of at least 50 ppm; said companion animal pet food composition meeting ordinary nutritional requirements for an adult canine.

17. A companion animal pet food composition comprising an antioxidant component that comprises (a) alpha-lipoic acid in an amount of about 100 ppm to about 200 ppm, (b) L-carnitine in an amount of about 400 ppm to about 600 ppm, (c) vitamin E in an amount of about 500 ppm to about 1000 ppm, and (d) vitamin C in an amount of at least 50 ppm; said companion animal pet food composition meeting ordinary nutritional requirements for an adult feline.

\* \* \* \* \*